(12) United States Patent
Flower

(10) Patent No.: US 7,364,574 B2
(45) Date of Patent: Apr. 29, 2008

(54) COMBINED PHOTOCOAGULATION AND PHOTODYNAMIC THERAPY

(75) Inventor: Robert Flower, Hunt Valley, MD (US)

(73) Assignee: Novadaq Technologies Inc., Ontario (CA)

( * ) Notice: Subject to any disclaimer, the term of this patent is extended or adjusted under 35 U.S.C. 154(b) by 0 days.

(21) Appl. No.: 10/619,548

(22) Filed: Jul. 16, 2003

(65) Prior Publication Data

US 2004/0206364 A1 Oct. 21, 2004

Related U.S. Application Data

(60) Provisional application No. 60/396,146, filed on Jul. 17, 2002.

(51) Int. Cl.
*A61F 9/008* (2006.01)

(52) U.S. Cl. ............... 606/4; 128/898; 607/88

(58) Field of Classification Search ............... 128/898; 606/4–6; 607/88–89
See application file for complete search history.

(56) References Cited

U.S. PATENT DOCUMENTS

| | | | |
|---|---|---|---|
| 5,279,298 A | 1/1994 | Flower | |
| 5,394,199 A | 2/1995 | Flower | |
| 5,576,013 A | 11/1996 | Williams et al. | |
| 5,707,986 A * | 1/1998 | Miller et al. ............... | 514/185 |
| 5,756,541 A | 5/1998 | Strong et al. | |
| 5,910,510 A | 6/1999 | Strong et al. | |
| 5,935,942 A * | 8/1999 | Zeimer ............... | 514/63 |
| 6,140,314 A * | 10/2000 | Zeimer ............... | 514/63 |
| 6,162,242 A | 12/2000 | Peyman | |
| 6,186,628 B1 | 2/2001 | Van de Velde | |
| 6,248,727 B1 * | 6/2001 | Zeimer ............... | 514/63 |
| 6,319,273 B1 * | 11/2001 | Chen et al. ............... | 607/88 |
| 6,351,663 B1 | 2/2002 | Flower et al. | |
| 6,351,667 B1 | 2/2002 | Godie | |
| 6,440,950 B1 | 8/2002 | Zeimer | |
| 6,443,976 B1 | 9/2002 | Flower et al. | |
| 6,840,933 B1 | 1/2005 | Pang et al. | |
| 6,936,043 B2 * | 8/2005 | Peyman ............... | 606/4 |
| 2002/0099279 A1 | 7/2002 | Pfeiffer et al. | |
| 2003/0060718 A1 * | 3/2003 | Alam et al. ............... | 600/476 |
| 2003/0060722 A1 | 3/2003 | Pfeiffer et al. | |
| 2003/0093064 A1 * | 5/2003 | Peyman ............... | 606/4 |
| 2003/0093065 A1 * | 5/2003 | Peyman ............... | 606/4 |

FOREIGN PATENT DOCUMENTS

WO          WO 00/47107        *   8/2000

OTHER PUBLICATIONS

Flower, Robert W., "Experimental Studies of Indocyanine Green Dye-Enhanced Photocoagulation of Choroidal Neovascularization Feeder Vessels", American Journal of Ophthalmology, vol. 129, No. 4, pp. 501-512, Elsevier Science Inc., 2000.
Flower, Robert W., "Optimizing Treatment of Choroidal Neovascularization Feeder Vessels Associated With Age-related Macular Degeneration", American Journal of Ophthalmology, vol. 134, No. 2, pp. 228-239, Elsevier Science Inc., 2002.

* cited by examiner

*Primary Examiner*—Henry M. Johnson, III
(74) *Attorney, Agent, or Firm*—Rissman Jobse Hendricks & Oliverio

(57) ABSTRACT

A method for treating a lesion of an animal, the animal having at least one vessel that carries blood to the lesion, comprising locating the vessel, administering a composition comprising a photodynamic agent, applying energy to the vessel to photocoagulate the vessel and thereby reduce the rate at which the treatment composition exits said lesion and applying energy to said lesion, of a type and an amount sufficient to excite the photodynamic agent, causing the lesion to undergo photodynamic therapy. Preferably, a dye that is both a fluorescent dye and a radiation absorbing dye, such as indocyanine green dye, is added to the treatment composition to allow (a) confirmation of the presence of the treatment composition in the lesion to be detected by fluorescent angiography and (b) the rate of blow flow to be reduced in the blood vessel feeding the lesion using dye enhanced photocoagulation.

14 Claims, 2 Drawing Sheets

COMBINED PHOTOCOAGULATION AND PHOTODYNAMIC THERAPY

This application claims priority from U.S. Patent Application No. 60/396,146, filed Jul. 17, 2002.

This invention relates to a method for treating lesions, and more specifically where said lesion is an age related macular degeneration associated choroidal neovascularization, wherein said neovascularization is supplied by at least one blood vessel.

BACKGROUND OF THE INVENTION

Lesions are normally defined as an abnormal tissue structure located in an organ or other body part, and are often a manifestation of a harmful condition, disease or illness. Lesions may take many specific forms, such as choroidal neovascularizations ("CNVs") which are found in the eye. In general, any abnormal vasculature in a body is a type of lesion.

Lesions must often be identified and visualized prior to treatment and such methods are known in the art. For example, CNVs are routinely visualized using indocyanine green ("ICG") dye angiography ("ICGA"). It is based on use of the near-infrared fluorescent light wavelengths emitted by ICG, which readily penetrate the pigmented ocular tissues. Methods for enhancing visualization of CNVs (i.e. as taught in U.S. Pat. No. 5,394,199) are also known in the art.

Traditionally, CNVs were treated by destruction of the entire CNV membrane using photocoagulation. Photocoagulation involves the application of energy, such as through a laser, sufficient to reduce the flow of blood through a target vessel or tissue. Photocoagulation of an entire CNV, however, involved the destruction of a significant portion of the retina. Advances in the visualization of CNVs allowed for the ability to perform high-speed imaging. This led to the development of a current AMD treatment modality, namely CNV feeder vessel photocoagulation treatment.

Following visualization of a CNV feeder vessel (e.g. by ICGA), feeder vessel photocoagulation is performed by photocoagulating an afferent vessel supplying blood to a CNV. This reduces or stops the flow of blood to the CNV. With feeder vessel photocoagulation, an often smaller fundus area is photocoagulated since only the feeder vessel is targeted even when the CNV itself may be relatively large in area. Also, the photocoagulation is often removed from the CNV, which may be juxta- or sub-foveal, thereby avoiding photocoagulation related damage to the fovea.

One feeder vessel photocoagulation methodology also involves the use of a radiation absorbing dye, such as ICG. The presence of the radiation absorbing dye in a target blood vessel enhances the uptake of near-infrared laser energy and decreases the amount of laser energy required to photocoagulate the targeted vessel and is referred to as Dye-Enhanced Photocoagulation ("DEP"). Thus, DEP reduces the amount of concomitant damage to the overlying sensory retina.

Another example of a current method for treating abnormal vasculature is photodynamic therapy ("PDT"). Generally, application of PDT requires administration of a photodynamic agent into a subject, typically by intra-venous injection. Once the agent arrives in a target site containing a tissue to be treated, the site is subjected to energy, e.g. light of a certain wavelength generated by a laser causing excitation of the agent. When the agent is excited, it produces oxygen radicals which then attack the cells of the surrounding tissue, resulting in degradation of those cells. By way of example, and in the case of CNV, PDT destroys vascular endothelial cells of the CNV. This reduces, and preferably halts, the flow of blood within the CNV.

It is possible that in some cases, reperfusion occurs following initially successful PDT of a CNV. PDT treatment may thus require multiple applications. Moreover, it now appears that the extent to which many PDT agents are selective for abnormal vasculature may not be as high as originally expected. In other words, concentration of PDT agent in the blood, rather than binding of PDT agent to the endothelium, is more determinative of efficacy of PDT treatment. As a result, the non-target areas of the fundus may be subjected to more PDT-mediated damage than originally anticipated. Also, PDT therapy traditionally involves infusing the PDT agent into a subject's vasculature, typically over about a ten (10) minute period. Infusion requires large quantities of PDT agent. Large quantities of PDT agent also translate into an increase in the likelihood of side effects, higher total cost and more light sensitivity post-treatment.

A need exists for improved methods of treatment of age-related macular degeneration associated choroidal neovascularizations and lesions generally.

SUMMARY OF THE INVENTION

The present invention provides a more effective method for treating lesions, in an animal. The method of the present invention utilizes photocoagulation and PDT methodologies. One broad aspect of the inventive method contemplates treating a lesion by locating at least one vessel that supplies blood to the lesion, administering a treatment composition comprising a photodynamic agent to the subject, performing photocoagulation of said blood vessel to reduce the rate of blood flow through said blood vessel and thereby reduce the rate at which said treatment composition exits said lesion, and then performing PDT by exposing the lesion to radiation of an amount and type sufficient to activate the photodynamic agent and subject the lesion to PDT-mediated damage. In one embodiment of the invention, the method is used to treat AMD-related CNVs.

Preferably, at least the partial presence of the PDT agent in the lesion is confirmed or approximated prior to photocoagulation of the feeder vessels. In one embodiment, this approximation or confirmation is carried out by administering a fluorescing dye and taking at least one angiogram.

In another embodiment of the invention, a radiation absorbing dye is administered prior to photocoagulation of said blood vessel to improve said photocoagulation by using dye-enhanced photocoagulation.

In a preferred embodiment of the invention, the photodynamic agent is administered along with a second dye that is both a fluorescing dye and a radiation absorbing dye, such as ICG, to treat AMD-related CNVs in a human.

Also provided is a system for treating lesions implementing one preferred embodiment of the inventive method.

One advantage of the present invention is that by cutting off the blood flow using photocoagulation or DEP after administration of the PDT agent, the PDT agent becomes incarcerated in the lesion. This is significant as PDT agents, such as Visudyne™, were previously thought to be held in the lesion during treatment because they were selectively bound to lesion tissues. However, it has come to light that PDT agents may not be as selectively bound to lesion tissues, such as CNVs, as originally anticipated. Therefore, by cutting off the blood flow to the lesion, once it has become at least partially filled with PDT agent, the PDT agent is physically held in the lesion for and during PDT.

A further advantage is that the incarceration of the PDT agent in the lesion also allows the PDT agent in non-lesion areas to be flushed out at higher flush-out rates as compared to lesion areas. As a result, non-lesion areas will be subjected to less PDT mediated damage while maintaining PDT agent in the lesion area.

A still further advantage is that the incarceration of PDT agent in the lesion increases the concentration of PDT agent in the lesion during treatment. A higher concentration of PDT agent in the lesion allows for more effective treatment.

A still further advantage is that given that the PDT agent can be effectively concentrated in the lesion, the overall amounts of PDT agent used can be lowered. In the instance where PDT agent is infused, infusion time can therefore be correspondingly lowered. This is economically advantageous and decreases the likelihood of side effects resulting from the PDT agent.

A still further advantage is that the reduction of blood flow through the feeder vessel enhances the rate of PDT-induced clot formation during PDT by reducing the movement and flow of blood through the lesion.

A still further advantage is that, in the case of AMD-related CNV, post-PDT sensitivity to sunlight is significantly greatly reduced because of greatly reduced quantities of administered PDT agent.

DETAILED DESCRIPTION OF THE PREFERRED EMBODIMENTS

In the following description, numerous specific details are set forth to provide a thorough understanding of the invention. However, it is understood that the invention may be practiced without these specific details. In other instances, well-known processes have not been described or shown in detail in order not to obscure the invention.

The methods of the present invention are claimed and described herein as a series of treatment steps. It should be understood that these methods and associated steps may be performed in any logical order that preserves the spirit of the invention. Moreover, the methods may be performed alone, or in conjunction with other procedures and treatments administered before, during or after such methods and steps set forth herein without departing from the scope and spirit of the invention. Further, it is contemplated that the term animals as used herein includes, but is not limited to, humans.

Achieving even more effective treatment of lesions, such as AMD-related CNV, lies in combining photocoagulation (or DEP) with PDT treatment methodologies.

Figure 1:
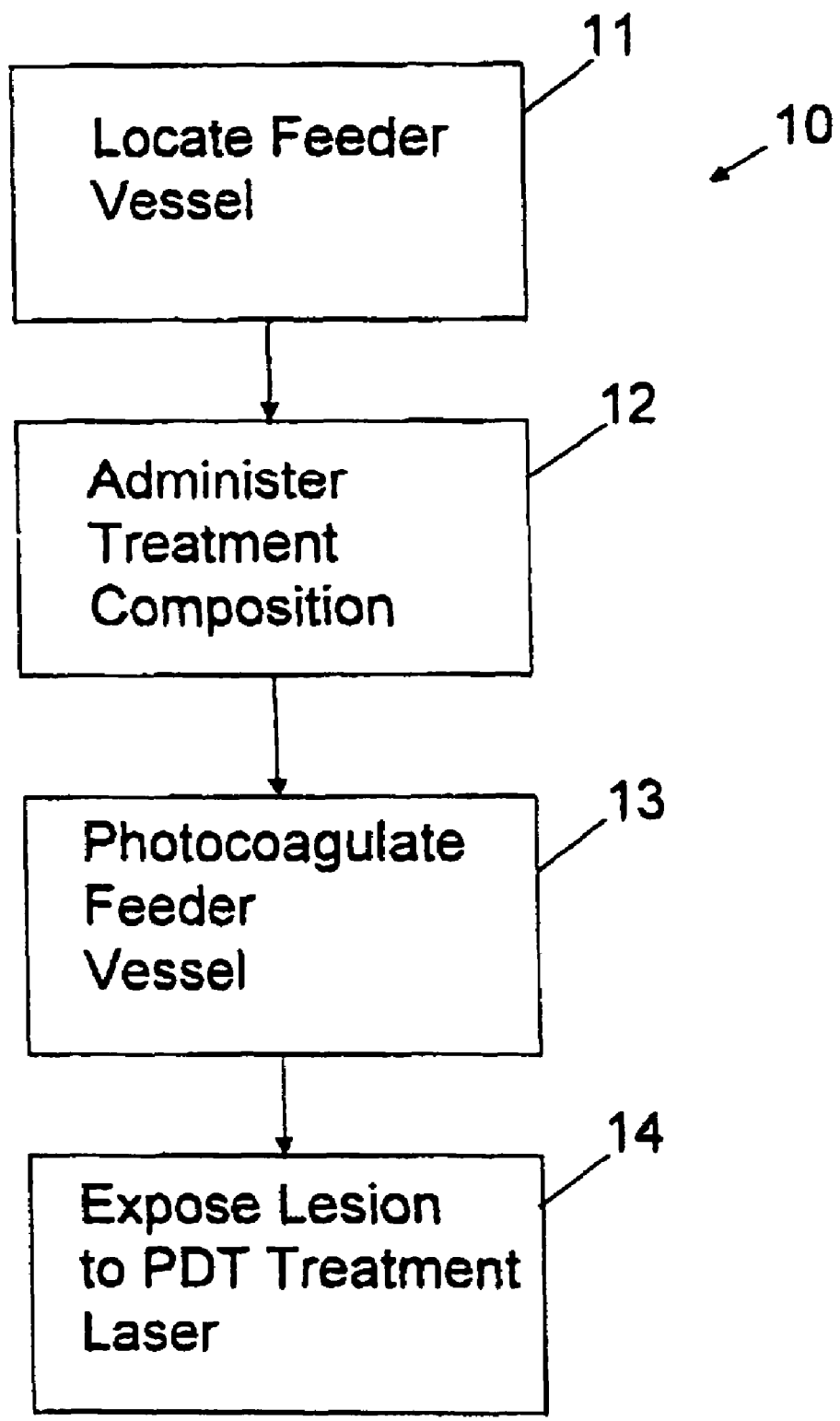
FIG. 1 illustrates, in flow chart form, a method for treating a lesion.

Referring to FIG. 1, a method for treating lesions according to one broad aspect of the invention is shown 10. The lesion should further have a blood vessel that carries blood into the lesion. The method 10 includes the following steps. Locating a feeder vessel associated with a lesion 11. Administering a composition comprising a photodynamic agent to the animal to fill at least a portion of the lesion with the composition 12. Energy, such as a first treatment light, is then applied to the feeder vessel, of sufficient type and amount to photocoagulate the feeder vessel thereby reducing the rate of blood flow in the feeder vessel and decreasing the rate at which the composition exits the lesion 13. PDT is then performed by exposing the lesion to energy, such as a second treatment light, of a type and amount sufficient to excite the photodynamic dye 14. Reducing, including stopping all together, the rate at which the composition, containing the PDT agent, exits a lesion is also referred to as "incarcerating", "holding", "maintaining", "sequestering" or "trapping" the PDT agent in the lesion. Further, it is understood that when referring to incarcerating the composition in the lesion, it is not necessary that all of the administered composition be incarcerated, but merely a proportion thereof.

In a preferred embodiment of the invention, the inventive method is used to treat AMD related CNVs.

In one embodiment of the invention, locating a feeder vessel of a lesion 11 is accomplished by administering a fluorescent dye to an animal, applying energy of a type and amount sufficient to cause said dye to fluoresce, and obtaining at least one angiogram of a pre-selected area of interest containing the lesion. In a further embodiment of the invention, a CNV and its associated feeder vessels are visualized using Indocyanine Green Dye Fluorescence Angiography. ICG dye is administered to a subject intravenously and allowed to perfuse through the subject's vasculature. Visualization is preferably effected by irradiating a pre-selected area, containing the CNV, with a laser light of a type and in an amount sufficient to cause the ICG dye to fluoresce.

A preferred dosage of ICG, for visualizing CNV feeder vessels, is about 7.5 mg administered at a concentration of about 25 mg/ml in a volume of approximately 0.3 ml administered intravenously. Only one bolus is required per imaging sequence but multiple boluses may be employed. A concentration of about 0.025 mg/ml in blood theoretically produces the most fluorescence from the fundus of a mammalian eye. Additionally, in some embodiments of the invention, administration of ICG intravenously is followed by a 5 ml saline flush. The saline flush is used to rapidly push the bolus out of the cubital vein and into the thoracic cavity.

Activation of ICG dye is preferably effected using a laser light source in the range of about 780 nm-830 nm. When visualizing a CNV and its associated feeder vessels in a mammalian eye, laser light used to excite dye fluorescence preferably irradiates a target site of about 1 cm$^2$. Irradiation is preferably effected by irradiating the target area for about 10-20 seconds with a 1-4 ms pulse every 40 ms, each pulse having a peak power of about 300 mW to 700 mW. Typically, about 10 mW to 40 mW of average power is used.

Capturing images of the fluorescing vasculature can be accomplished by numerous means which are known and will be apparent to a person skilled in the art. Images are preferably captured as high speed angiographic images on a CCD camera. The resultant images are analyzed to identify a lesion and feeder vessels associated with that lesion.

While the above represents preferred parameters for visualizing a CNV and identifying associated feeder vessels, it is well known in the art that other dosages are also effective to produce fluorescence in the eye such that a CNV and its associated feeder vessels can be identified and located.

Following the locating of a feeder vessel associated with a lesion, a composition comprising a photodynamic dye is administered to the subject 12. The photodynamic dye can be one or a combination of any of a number of available photodynamic agents. The agent selected should be capable of causing damage to a targeted tissue after exposure to an appropriate type of radiation, e.g. light of a certain wavelength, typically between about 630 nm and about 750 nm. Many dyes that meet these criteria are available, and include, but are not limited to the following dyes, some of which are enumerated in U.S. Pat. No. 6,443,976:

hematoporphyrins, which include derivatives thereof such as, e.g. dihematoporphyrins ethers and dimer and trimers of hematoporphyrins (examples of which are described in U.S. Pat. Nos. 4,968,715 and 5,190,966), and improvements thereon, examples of the latter being described in U.S. Pat. Nos. 5,028,621, 4,866,168, 4,649,151 and 5,438,071;

aminolevulinic acids (precursors to hematoporphyrin) as sources of photodynamic compounds, as described and exemplified in U.S. Pat. No. 5,079,262;

porphyrins, including boronated porphyrin, benzoporphyrin, and derivatives thereof, and as further exemplified by the green porphyrin described in U.S. Pat. Nos. 4,883,790, 4,920,143, 5,095,030 and 5,171,749;

mercocyanines;

porphycenes;

porfimer sodium;

indocyanine green verteporfin (Visudyne™, CIBA Vision);

Photofrin II™;

PH-10™;

chlorins, as exemplified by meso-tetra(hydroxyphenyl)-chlorin and bacteriochlorins, the latter exmplified in U.S. Pat. Nos. 5,171,741, 5,173,504;

zinc phthalocyanine, as described in U.S. Pat. No. 5,166,197;

purpurins, such as tin ethyl etiopurpurin (SnET2™, Miravant);

pheophorbides, examples of which are described in U.S. Pat. Nos. 5,198,460, 5,002,962 and 5,093,349; and monoclonal antibody-dye conjugates of each of the foregoing.

In one preferred embodiment, Visudyne™ is used as the photodynamic agent when treating a CNV in a human or mammalian eye. In some embodiments of the invention, the photodynamic agent is administered along with a pharmaceutically acceptable carrier.

The dose of photodynamic dye to be administered is that amount sufficient to, upon excitation, damage a specific target tissue. Given the various acceptable ways that a photodynamic agent can be administered to a subject, including, but not limited to delivery via liposomes or intravenous injection, a dosage will vary accordingly. A preferred dosage of photodynamic agent will therefore depend on mode of delivery, type of agent, and composition.

In one embodiment of the invention, 15 mg of Visudyne™ is diluted in 7.5 ml to produce a 2 mg/ml solution. Dose for a subject is then calculated on the basis of surface area of 6 mg/m$^2$. Based on this, the appropriate amount is extracted from Visudyne™ solution and is diluted to 30 ml with 5% dextrose solution. The 30 ml of Visudyne™ solution is then infused over 8 minutes into the subject's vasculature.

In another embodiment of the invention, the photodynamic agent is delivered as a rapid bolus intravenously. Additionally, in this embodiment of the invention, administration of PDT agent is followed by a 5 ml saline flush. The saline flush is used to rapidly push the bolus out of the cubital vein and into the thoracic cavity.

In one preferred embodiment of the invention, after administering the PDT agent but prior to photocoagulation of the feeder vessel, at least the partial presence of the PDT agent in the lesion is confirmed or at least approximated. This can be achieved by administering a fluorescing dye separately or along with the photodynamic agent but prior to photocoagulation of the feeder vessel. Such dye is effective for fluorescence angiography and includes, but is not limited to, ICG. Energy sufficient to fluoresce the dye is applied and at least one angiographic image is then captured.

If the fluorescing dye is administered along with the PDT agent in the same treatment composition (i.e. as part of the same bolus or infusion mixture), then subsequent fluorescent angiography will show the presence of that bolus or mixture (and thus the PDT agent) in the lesion as indicated by fluorescence within said lesion. If the fluorescing dye is administered separately from the PDT agent, the presence of the PDT agent in the lesion can also be approximated by calculating the arrival of the PDT agent in the lesion depending on the pre-determined time lapse between the administration of the PDT agent and fluorescing dye.

In another preferred embodiment of the invention, a radiation absorbing dye is used prior to photocoagulation of the feeder vessel. Such dye is effective for dye enhanced photocoagulation and includes, but is not limited to, ICG. The radiation absorbing dye can be administered separately or along with the photodynamic agent.

In treating CNVs, Visudyne™ is preferably combined with ICG dye such that a 0.3 ml formulation has final concentration of about 65 mg/ml ICG. Intravenous administration of the bolus is followed by a 5 ml saline flush. Advantageously, ICG is both a fluorescing and radiation-absorbing dye. By irradiating the fundus of the eye with radiation sufficient to fluoresce the ICG dye, the practitioner can approximate or confirm the presence of the combined ICG/PDT agent formulation in the CNV while ICG also being effective for subsequent DEP. While these represent preferred values for a combined Visudyne™ and ICG bolus, it will be understood by those skilled in the art that other values are permissible and effective.

Following administration of a photodynamic agent such that the lesion is at least partially filled with an effective amount of photodynamic agent, photocoagulation of the feeder vessel of the lesion is performed 13. Targeting of a photocoagulation treatment beam is based upon information previously derived from the locating of the feeder vessel associated with the lesion. Photocoagulation is effected by applying radiation of a kind and amount sufficient to effect an occlusion of a target feeder vessel. It is believed that such occlusion occurs by increasing the temperature of the feeder vessel, resulting in either cauterization of the feeder vessel or clotting of the blood within the feeder vessel. As a result, the rate of blood flow through the feeder vessel is reduced. Photocoagulation of a vessel results in the reduction in the rate of blood flow through such vessel, this includes but is not limited to halting blood flow completely.

In embodiments of the invention where a radiation absorbing dye is administered, enhanced photocoagulation of the feeder vessel is effected by utilizing DEP. In the preferred embodiment wherein a combined bolus of ICG dye and Visudyne™ is administered, photocoagulation is enhanced by utilizing the radiation absorbing properties of the ICG dye to perform DEP of the feeder vessel. Thus, in this embodiment, ICG can act as both the fluorescing dye and the radiation-absorbing dye. Preferably, an approximately 810 nm treatment laser is used at about 400-600 mW for about 1.0-1.5 seconds to effect ICG DEP. This produces about 0.4 J-0.9 J of energy sufficient to photocoagulate the vessel in the presence of ICG.

By photocoagulating a feeder vessel that supplies blood into a lesion just after the photodynamic agent has at least partially filled the lesion, the photodynamic agent is incarcerated in the lesion since the rate of fluid flow though the feeder vessel is reduced and thus the rate at which the PDT agent exits the lesion is also reduced.

ICG is known to also have some photodynamic properties. Thus, in some embodiments of the invention, ICG is used as a photodynamic agent, fluorescing dye and a radiation-absorbing dye.

The photodynamic agent, fluorescing dye and the radiation-absorbing dye may each be delivered separately as rapid boluses intravenously, as a rapid single bolus, each infused over a defined period of time, or any combination thereof without departing from the spirit of the invention.

Photodynamic therapy is then performed on the lesion 14. The target tissue is irradiated with radiation of a type and amount sufficient to excite the PDT agent and damage the lesion. Thus, the radiation excites the PDT agent, now incarcerated in the lesion, effecting PDT treatment of the lesion.

In one embodiment of the invention, after photocoagulation of the feeder vessel but prior to PDT, there is an additional step of confirming that the rate at which PDT exits the lesion has been reduced. In those embodiments where a fluorescing dye was administered along with the PDT agent, this confirmation can be achieved by applying energy to the area of the lesion and obtaining a subsequent angiographic image. If the PDT agent/fluorescing dye mixture is incarcerated in the lesion, vessels outside of the lesion will be subjected to regular flush out rates. Thus, the angiographic image will show fluorescence for vessels within the lesion with a marked decrease in fluorescence in vessels outside the lesion. In those embodiments where no fluorescing dye was administered prior to photocoagulation, then confirmation can be achieved by first administering a fluorescing dye before applying the appropriate energy to fluoresce the dye and obtaining a subsequent angiographic image. In this case, since the feeder vessel has been photocoagulated, the newly administered fluorescing dye will not be able to enter the lesion (or at least enter at a reduced rate). Thus, the angiographic image will show fluorescence for vessels outside the lesion with a marked decrease in fluorescence in vessels within the lesion.

Typical parameters for photocoagulation, DEP and PDT have been provided as preferred values and should not be construed as a limitation on the claims of the present invention. It will be apparent to those skilled in the art that other parameters are permissible and effective to work the invention.

A lesion is therefore attacked on two fronts. First, the lesion's blood supply is cut off using photocoagulation or DEP. This has the effect of starving the lesion and immediately reducing the hemodynamic pressure. Second, the abnormal vasculature itself is targeted by PDT. Excitation of the photodynamic agent present in the lesion additionally damages the lesion directly.

This combined photocoagulation (preferably DEP)/PDT is not a simple serial application of both PDT and DEP, but an integrated method. This integrated method, consisting of PDT and DEP methodologies in a predetermined order has new and unanticipated results, when compared to PDT and DEP performed separately.

Photocoagulation is performed after at least one feeder vessel associated with a lesion has been identified and a photodynamic agent has been administered, but before application of PDT treatment radiation. Only after photocoagulation of the feeder vessel is the PDT radiation applied to a predetermined treatment area containing the lesion to effect activation of the PDT agent.

Significantly, the present invention of combined photocoagulation and PDT as outlined has several advantageous effects over and above the additive effect of the individual therapies alone. As outlined, this combined therapy exhibits advantageous synergistic effects.

Figure 2:
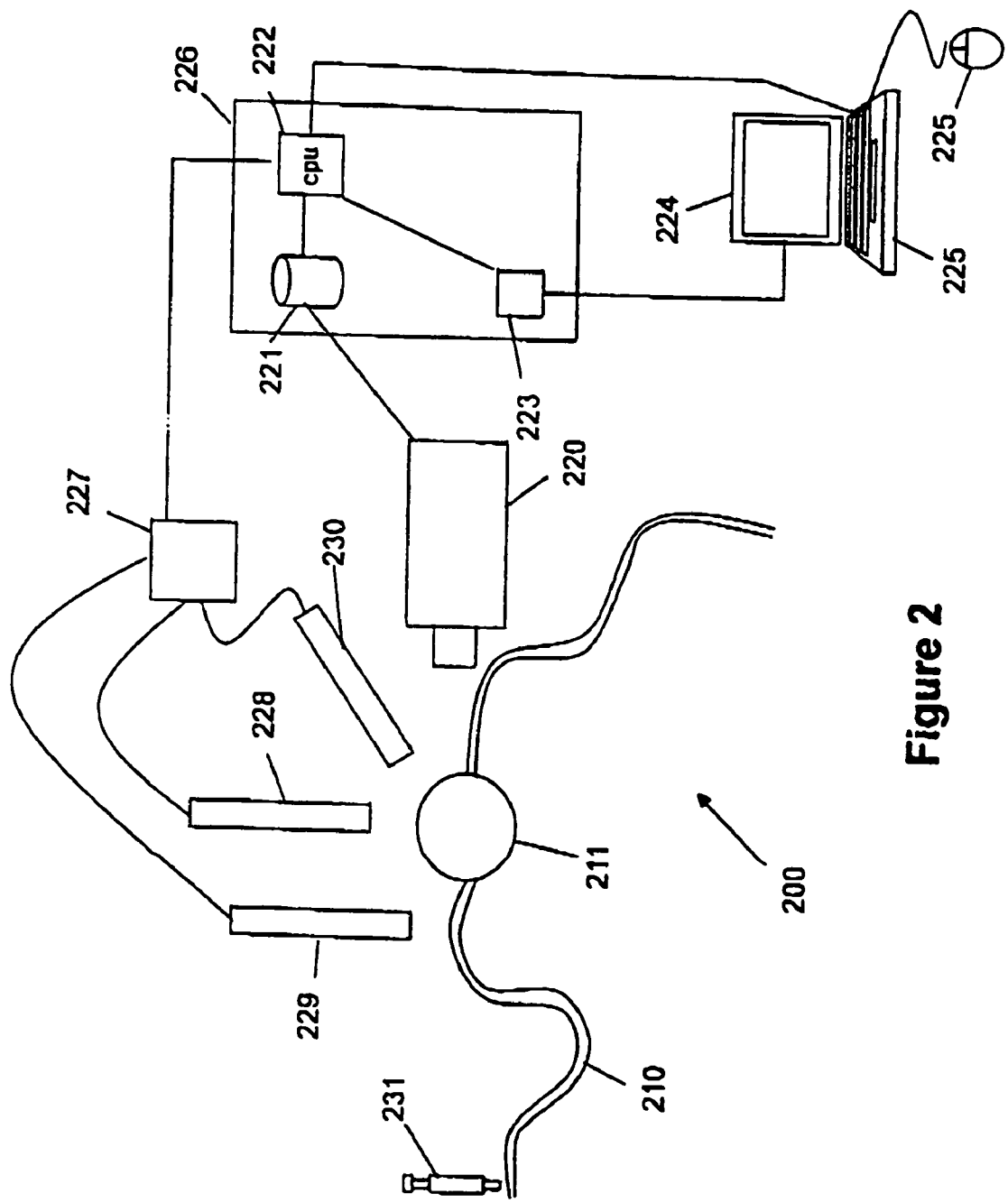
FIG. 2 illustrates an overall system diagram implementing one embodiment of the inventive method.

Referring to FIG. 2, a system 200 is provided for implementing one preferred embodiment of the inventive method. A tool for administering a composition intravenously such as a syringe 231 is provided. A lesion 211 is supplied by a feeder vessel 210, both shown magnified. A CCD camera 220 is provided. A computer system 226 comprises a CPU 222, memory 221, such as a hard disk and random access memory, an imaging processor 223, a PC monitor 224 and one or more input devices 225. A controller 227 is provided. A first laser 230, a second laser 229 and a third laser 228 are provided.

In practice, the identification of the feeder vessel 210 is carried out by injecting a patient intravenously with a fluorescent dye, preferably ICG, using the syringe 231. Energy, of a type and amount sufficient to cause the fluorescent dye in the blood vessels, in and around the lesion 211, to fluoresce, is applied using the first laser 230. The first laser 230 is controlled by the controller 227 that receives input signals from the CPU 222. At least one angiographic image, of the fluorescing lesion 211 and the surrounding area, is then taken using the CCD camera 220. Said angiographic image is stored in memory 221 and displayed on the monitor 224 using an imaging processor 223, thus allowing a feeder vessel 210 to be identified.

A treatment composition, comprising a PDT agent and ICG dye is then administered intravenously using a syringe 231. The presence of the treatment composition in the area corresponding to the lesion 211 and the feeder vessel 210, is confirmed by applying energy, using the first laser, of a type and amount sufficient to cause the ICG in the blood vessels of the lesion 211 and the feeder vessel 210 to fluoresce. An angiographic image is then taken using the CCD camera 220 and displayed on the monitor 224 as described above.

The feeder vessel 210 is then photocoagulated by applying energy, of a type and amount sufficient to reduce the rate of blood flow through said feeder vessel 210, using the second laser 229. The second laser 229 is controlled by the controller 227 which receives input signals from the CPU 222.

The lesion 211 is then subjected to PDT by applying energy, of a type and amount sufficient to excite said PDT agent, using the third laser 228. The third laser 228 is controlled by the controller 227 which receives input signals from the CPU 222.

Although the invention has been described with reference to certain specific embodiments, various modifications thereof will be apparent to those skilled in the art without departing from the spirit and scope of the invention as outlined in the claims appended hereto.

The embodiments of the invention in which an exclusive property or privilege is claimed are defined as follows:

1. A method for treating a lesion in an animal, said animal having at least one blood vessel that carries blood to said lesion, comprising:
   (i) locating said blood vessel;
   (ii) administering a treatment composition comprising a dye and a photodynamic agent selected from the group consisting of hematoporphyrin, an aminolevulinic acid, a porphyrin, a mercocyanine, a porphycene, porfimer sodium, a verteporfin, Photofrin II™, PH-10™, a chlorin, a zinc phthalocyanine, a purpurin, and a pheophorbide, said photodynamic agent being suitable for photodynamic therapy;

(iii) after step (ii), applying energy to said blood vessel, of a type and in an amount sufficient to reduce or stop the rate of blood flow through said blood vessel thereby reducing the rate at which said treatment composition exits said lesion; and (iv) irradiating said dye to confirm that the lesion is at least partially filled with said treatment composition;

(iv) after step (v), applying energy to said lesion, of a type and in an amount sufficient to excite said photodynamic agent.

2. The method of claim 1, wherein the animal is a human.

3. The method according to claim 1, wherein said lesion is an age related macular degeneration associated choroidal neovascularization in a human.

4. The method according to claim 1, wherein said treatment composition is administered intravenously as a bolus.

5. The method according to claim 4, wherein said intravenous administration of said treatment composition is followed by intravenously administering a saline flush.

6. The method according to claim 1, wherein said treatment composition is administered by intravenously infusing said treatment composition over a predefined time interval.

7. The method according to claim 1, wherein step (iii) is performed after a pre-defined time interval following step (ii).

8. The method according to claim 1, wherein said treatment composition is administered using a heat-sensitive liposomes.

9. The method according to claim 1, wherein said locating of said blood vessel is carried out using fluorescent dye angiography comprising:

(a) administering a visualizing composition comprising a fluorescent dye;

(b) applying energy of a type and in an amount sufficient to cause said fluorescent dye to fluoresce as said fluorescent dye flows through the blood vessel; and (c) obtaining at least one angiographic image of the fluorescent dye in the blood vessel sufficient to locate said blood vessel that carries blood into said lesion.

10. The method according to claim 9, wherein said fluorescent dye is indocyanine green dye.

11. The method according to claim 1, wherein said dye is indocyanine green dye.

12. The method according to claim 1, wherein:

(a) prior to step (iii), there is an additional step of administering a radiation absorbing dye suitable for dye-enhanced photocoagulation; and (b) thereby step (iii) results in dye enhanced photocoagulation of said blood vessel.

13. The method according to claim 12, wherein said administering of radiation absorbing dye is achieved by said radiation absorbing dye forming part of said treatment composition.

14. The method according to claim 1, wherein step (iii) comprises exciting a radiation-absorbing dye.

* * * * *

UNITED STATES PATENT AND TRADEMARK OFFICE
CERTIFICATE OF CORRECTION

PATENT NO. : 7,364,574 B2
APPLICATION NO. : 10/619548
DATED : April 29, 2008
INVENTOR(S) : Robert Flower Page 1 of 1

It is certified that error appears in the above-identified patent and that said Letters Patent is hereby corrected as shown below:

Column 9, line 11, in claim 1, (iv) after step (v), should read -- (v) after step (iv) --.

Column 9, line 30, delete "a" before "heat-sensitive liposomes".

Signed and Sealed this

Fifth Day of August, 2008

JON W. DUDAS
*Director of the United States Patent and Trademark Office*